United States Patent
Alley et al.

(10) Patent No.: US 6,185,447 B1
(45) Date of Patent: Feb. 6, 2001

(54) METHOD FOR TEMPORALLY RESOLVED, THREE-DIMENSIONAL MR VOLUME ACQUISITIONS

(75) Inventors: Marcus T. Alley, Palo Alto; Norbert J. Pelc, Los Altos, both of CA (US)

(73) Assignee: The Leland Stanford Junior University, Palo Alto, CA (US)

(*) Notice: Under 35 U.S.C. 154(b), the term of this patent shall be extended for 0 days.

(21) Appl. No.: 09/049,281

(22) Filed: Mar. 26, 1998

(51) Int. Cl.$^7$ .................................................. A61B 5/055
(52) U.S. Cl. ........................ 600/420; 324/307; 324/309
(58) Field of Search .................................. 324/307, 309; 600/420; 424/9

(56) References Cited

U.S. PATENT DOCUMENTS

| | | | |
|---|---|---|---|
| 4,707,658 | 11/1987 | Frahm et al. | 324/309 |
| 4,710,717 | 12/1987 | Pelc et al. | 324/309 |
| 5,377,680 | 1/1995 | Bernstein et al. | 128/653.2 |

OTHER PUBLICATIONS

Thomas K. Foo, Ph.D., et al., "Improved Ejection Fraction and Flow Velocity Estimates with Use of View Sharing and Uniform Repetition Time Excitation with Fast Cardiac Techniques", Radiology 1995; 195:471–478.

Dennis R. Wetter, MD et al., "Cardiac Echo–planar MR Imaging: Comparison of Single– and Multiple–shot Techniques", Radiology 1995; 194:765–770.

Martin Unterweger, MS et al., "Comparison of Echoplanar and Conventional Cine–Magnetic Resonance Data–Acquistion Strategies", vol. 29, No. 11, 994–1000.

*Primary Examiner*—Christine K. Oda
*Assistant Examiner*—Tiffany A. Fetzner
(74) *Attorney, Agent, or Firm*—Townsend and Townsend and Crew LLP; Henry K. Woodward

(57) ABSTRACT

Disclosed is an apparatus and a method for three dimensional magnetic resonance data acquisitions using a fast 3D sequence to acquire volumetric data in a cine mode. The entire heart can be imaged in the same amount of time that a conventional cine scan requires for a single section. The true temporal resolution is similar to that of the segmented k-space acquisition. The sequence uses very short repetition times (TR), and hence the inherent contrast is poor. This problem is overcome with the use of a $T_1$ shortening agent. Since contrast between blood and the myocardium is no longer flow dependent, it is more stable throughout the heart cycle.

11 Claims, 4 Drawing Sheets

METHOD FOR TEMPORALLY RESOLVED, THREE-DIMENSIONAL MR VOLUME ACQUISITIONS

The U.S. government has rights in the disclosed invention pursuant to NIH Contract F32 DK09232 with Stanford University, assignee.

BACKGROUND OF THE INVENTION

This invention relates generally to magnetic resonance data acquisition and imaging, and more particularly the invention relates to a three-dimensional magnetic resonance sequence for acquiring volumetric data depicting a motion cycle.

Cardiac MRI can provide extremely accurate measures of chamber volumes, stroke volume, cardiac output and ejection fraction. The most commonly used methods are cine MR (described in U.S. Pat. No. 4,710,717, "Method for Fast Scan Cine NMR Imaging," Norbert J. Pelc and Gary H. Glover, December, 1987), and segmented k-space techniques (described in U.S. Pat. No. 5,377,680, "MRI Cardiac Image Produced by Temporal Data Sharing," Tsur Bernstein and Thomas K. Foo, January, 1995). Both of these techniques employ two-dimensional (2D) data acquisition strategies, and have limitations. For example, a cine scan with 128 phase-encodings can image 3 slices with a temporal resolution of approximately 60 ms in roughly 2 minutes, but the need for volumetric coverage increases the total scan time substantially. The segmented k-space methods reduce the scan time at the expense of temporal resolution. They image a single slice in a breath-hold with 80 ms temporal resolution. However, the rest periods between scans makes the total scan time for volumetric coverage comparable to that in cine. Both techniques produce 2D image sets, which must be concatenated for volumetric measurements. Thus, any subject movement during the scan can lead to slice registration errors, which in turn can affect the quality of the results. With both techniques, it may be difficult to obtain high spatial resolution in the slice direction. Further, both methods can suffer from insufficient contrast between the blood in the chambers and the myocardium, especially during flow stasis in diastole. This makes automatic volumetric analysis difficult, and manual analysis is tedious and introduces measurement variability.

MRI techniques produce images of individual slices by encoding spatial information. In the most commonly used method, often called 2DFT or "spin-warp", location in one direction is encoded using selective excitation which generates signal only from a slice through the object. Location in a second direction is encoded by acquiring the signal in the presence of a magnetic field in that direction, thereby encoding position into the temporal frequency of the measured signal. Location in the third direction is encoded using a preparation "phase encoding gradient". To form an image, the sequence of pulses that form the pulse sequence must be repeated many times using many values of this phase encoding gradient. The time between sequence repetitions is called the repetition time TR.

The method described above forms an image of a single plane. Many such images to cover a volume can be acquired either sequentially or in an interleaved manner. It is also possible to acquire data from a 3D volume simultaneously. For example, one can generate signal using an excitation pulse that excites a relatively thick slab. Position in the slice direction along the slab is encoded using a second phase encoding gradient.

Imaging techniques which are faster than those described above are known. One, called Echo Planar Imaging (EPI) is even capable of forming an image of an entire slice from data acquired during a single pulse sequence execution. However, the image quality using "single shot EPI" may not be acceptable for some applications. For these, it is possible to use multi-shot EPI. Other fast imaging methods, e.g. spiral k-space scanning, are also known.

SUMMARY OF THE INVENTION

The present invention provides a fast 3D imaging sequence for acquiring volumetric data in a cine mode whereby the entire volume, e.g. the heart, can be imaged in a time comparable to that of a single cine scan with the temporal resolution being similar to that in a segmented k-space 2D acquisition.

Briefly, a body with cyclical motion such as the heart is placed in a magnetic field ($B_o$), and a plurality of data acquisition sequences are implemented using a common time marker, such as the heartbeat as determined by an electrocardiogram (ECG). The repetition time for each sequence is made very short. A phase encode rewinder gradient can be used to reduce artifacts, and RF spoiling and crusher gradients can be used to improve the suppression of static tissue.

In the preferred embodiment, data for different slice direction phase encode gradients are collected during each heart beat while the in-plane phase encode gradient remains constant.

The invention and objects and features thereof will be more readily apparent from the following description and appended claims when taken with the drawings.

DESCRIPTION OF THE ILLUSTRATIVE EMBODIMENTS

Figure 1A:
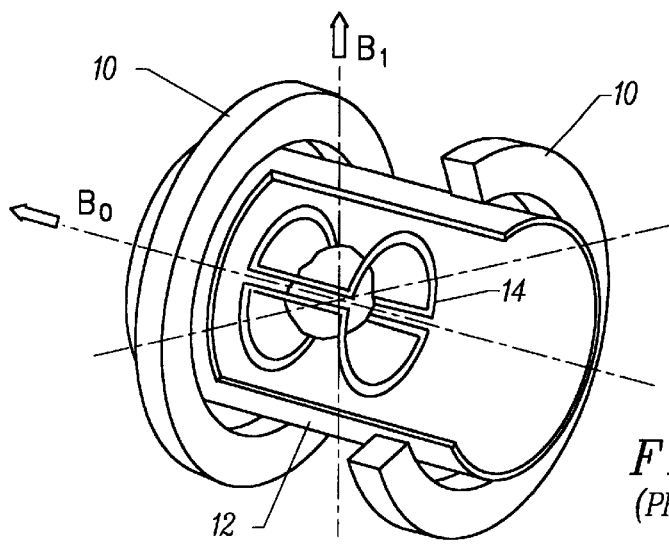
FIGS. 1A–1D illustrate the arrangement of conventional MRI apparatus and magnetic fields generated therein.
Figure 1B:
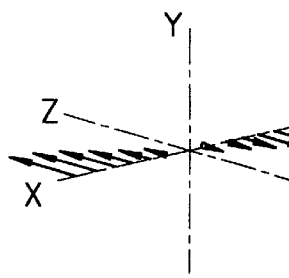
Figure 1C:
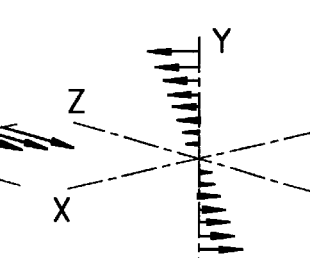
Figure 1D:
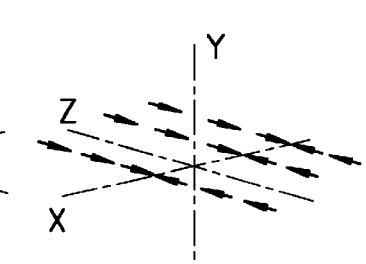

FIG. 1A is a perspective view, partially in section, illustrating coil apparatus in MR imaging system and FIGS. 1B–1D illustrate field gradients which can be produced in the apparatus of FIG. 1A. Briefly, the uniform static field $B_o$ is generated by the magnet comprising the coil pair 10. A gradient field G(x) is generated by a complex gradient coil set which can be wound on the cylinder 12. An RF field $B_1$ is generated by a saddle coil 14. A patient undergoing imaging would be positioned along the Z axis within in the saddle coil. In FIG. 1B an ideal X gradient field is shown which is parallel to the static field $B_o$ and varies linearly with distance along the X axis but does not vary with distance along the Y or Z axes. FIGS. 1C and 1D are similar representations of the Y gradient and Z gradient fields, respectively.

Figure 2:
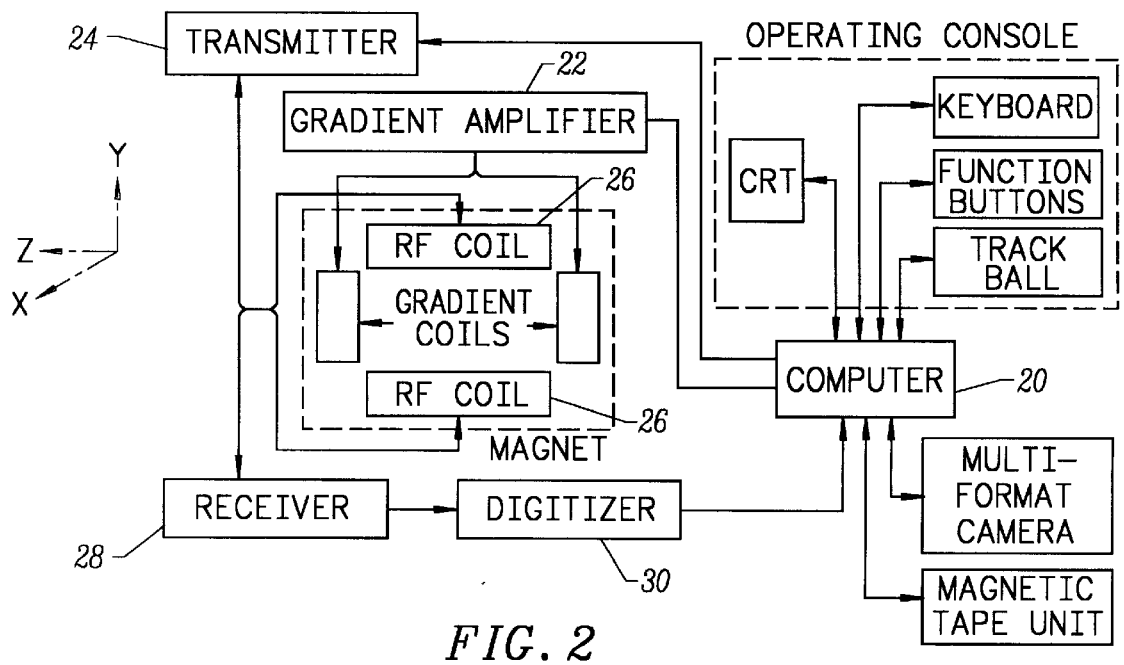
FIG. 2 is a functional block diagram of MRI imaging apparatus.

FIG. 2 is a functional block diagram of conventional imaging apparatus. A computer 20 was programmed to control the operation of the MRI apparatus and process FID signals detected therefrom. The gradient field is energized by a gradient amplifier 22 and the RF coils for impressing an RF magnetic moment which rotates at the Larmor frequency is controlled by the transmitter 24 and the RF coils 26. After the selected nuclei have been excited, the RF coils 26 are employed to detect the FID signal which is passed through the receiver 28 and then through digitizer 30 for processing by computer 20. For the dynamic imaging techniques of the present invention, physiological monitoring and triggering equipment (not shown) may be needed, as known by one skilled in the art.

The present invention provides a fast 3D sequence to acquire volumetric data in a cine mode. A large volume, perhaps covering the entire heart can be imaged in the same amount of time as a single cine scan. The temporal resolution is similar to that in a segmented k-space 2D acquisition. Table 1 compares the acquisition times between conventional cardiac cine imaging, a segmented k-space technique, an EPI-based approach, and the 3D cine sequence of the present invention. The same spatial resolution is considered in all four techniques.

TABLE 1

A comparison of acquisition times between four cine techniques.

|  | Conventional Cine | Segmented GRE | EPI | 3D Cine |
|---|---|---|---|---|
| Heart rate | 60 bpm | | | |
| Coverage | 16 10 mm sections | | | |
| In-plane FOV | 40 × 20 cm | | | |
| In-plane matrix | 256 × 72 | | | |
| TR (ms) | 20 | 10 | 40 | 5 |
| Temporal resolution (ms) | 80 | 80 | 40 | 80 |
| Heart Beats per scan | 72 | 9 | 5 | 72 |
| Sections acquired per RR | 4 | 1 | 1 | 16 |
| Acquisition time(s) | 288 | 144 | 80 | 72 |

While conventional cine requires a number of heart beats equal to the number of phase-encoding steps to image one section, the overall scan time can be reduced by simultaneously acquiring up to four sections in an interleaved manner. The segmented k-space sequence acquires 8 phase-encoding values per temporal phase, and thus 9 heart beats are required for each section. The true temporal resolution is equal to that of conventional cine. The EPI technique considered here collects k-space data over 5 heart beats, and offers an improved temporal resolution equal to that of the sequence TR. With both the segmented k-space and EPI methods breath-holding is used. The rest period between section acquisitions is not included in this table and will further increase the total acquisition time.

Figure 3:
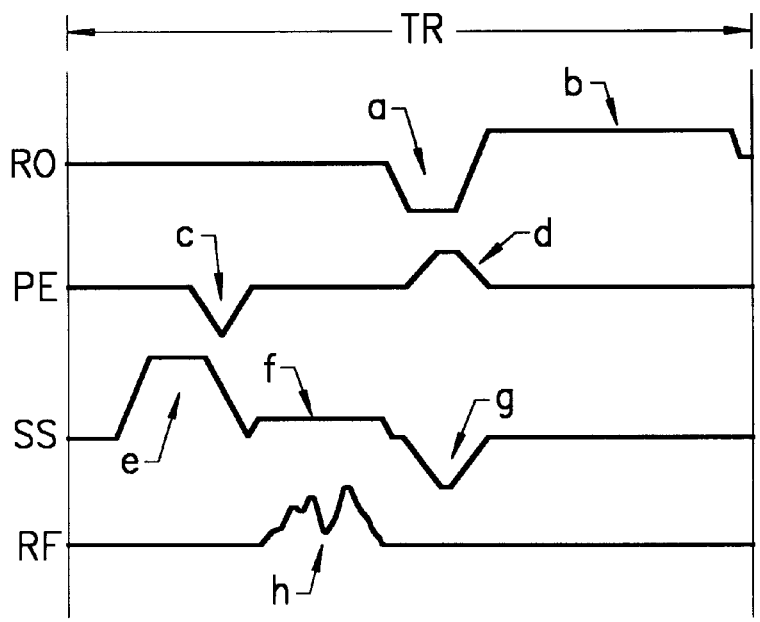
FIG. 3 illustrates a gradient-recalled echo data acquisition sequence for a short repetition time (TR) as used in one embodiment of the present invention.

To perform the volumetric data acquisition in accordance with the invention, the representative short TR gradient recalled data acquisition pulse sequence as shown in FIG. 3 is used. A very short TR is accomplished through several steps. The sequence design shown here assumes a scanner that is capable of gradients which rise to a full gradient amplitude of 22 mT/m in 184 µs. The slab excitation (f and g in FIG. 3) is performed with a 600 µs reduced power selective RF pulse (h; the RF phase waveform is not shown), and data are acquired using a receiver bandwidth of 64 kHz (the readout gradients are shown as waveforms a and b). First-order moment nulling is not used in order to keep the echo time (TE) as short as possible. The in-plane phase encode gradient is shown as waveform (d). An in-plane phase encode "rewinder" gradient used to reduce artifacts (waveform c represents the rewinder for the previous TR). RF spoiling and "crusher" gradients (e) are used to improve the suppression of static tissue.

Figure 4:
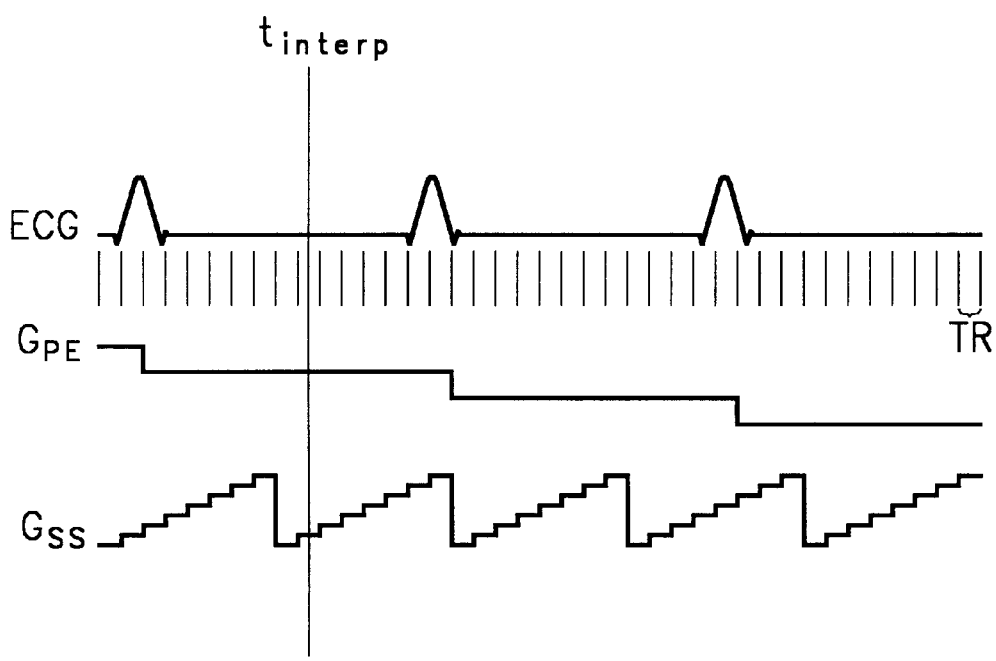
FIG. 4 illustrates repetitive 3D cine acquisition using the data acquisition sequence of FIG. 3 in accordance with the invention.

A schematic representation of the acquisition scheme is shown in FIG. 4. In FIG. 4, as in conventional cine imaging, the in-plane phase encoding ($G_{pe}$) is constant during each heart beat. The value of the in-plane phase encode ($G_{pe}$) changes with each RR interval, while the value of the slice direction phase encode ($G_{ss}$) changes with every TR interval. The data acquired for each in-plane and slice-direction phase-encoding are interpolated in time to produce data for each desired time frame ($t_{interp}$ in FIG. 4). Data at time $t_{interp}$ are constructed through linear interpolation of nearest neighbor points. All $N_z$ slice-direction phase encodings ($G_{ss}$) are interleaved in each heart beat, thereby achieving a temporal resolution of $N_z \times TR$. The scan time for $N_y$ in-plane phase-encodes is thus $N_y$ heart beats. Other interesting schemes can be used. For example, if the desired number of slice encoding $N_z$ is too large for the required temporal resolution, a fraction of the $N_z$ encodings can be used in any single heart cycle, the rest being used in another heart cycle. Also, some combination of y and z direction phase encodings could be interleaved.

Respiratory compensation is implemented by making the value of the in-plane phase-encode dependent on the respiration cycle. The method supports zero-padding in the slice-direction, which allows the production of overlapped slices. Partial k-space coverage of the in-plane or slice phase-encoded directions can also be used.

In this configuration the sequence TR and TE are typically 5.0 and 1.2 ms, respectively. A volume of 16 7.5 mm sections can be used to cover the entire heart. With this value of $N_z$, the true temporal resolution is 80 ms. Zero-filling by a factor of two in the slice direction will increase the number of reconstructed slices to 32 with no loss of temporal resolution or increase in acquisition time. With an in-plane phase encode resolution of 192, and a subject heart rate of 60 bpm, the total acquisition time is 3.2 min.

Figure 5:
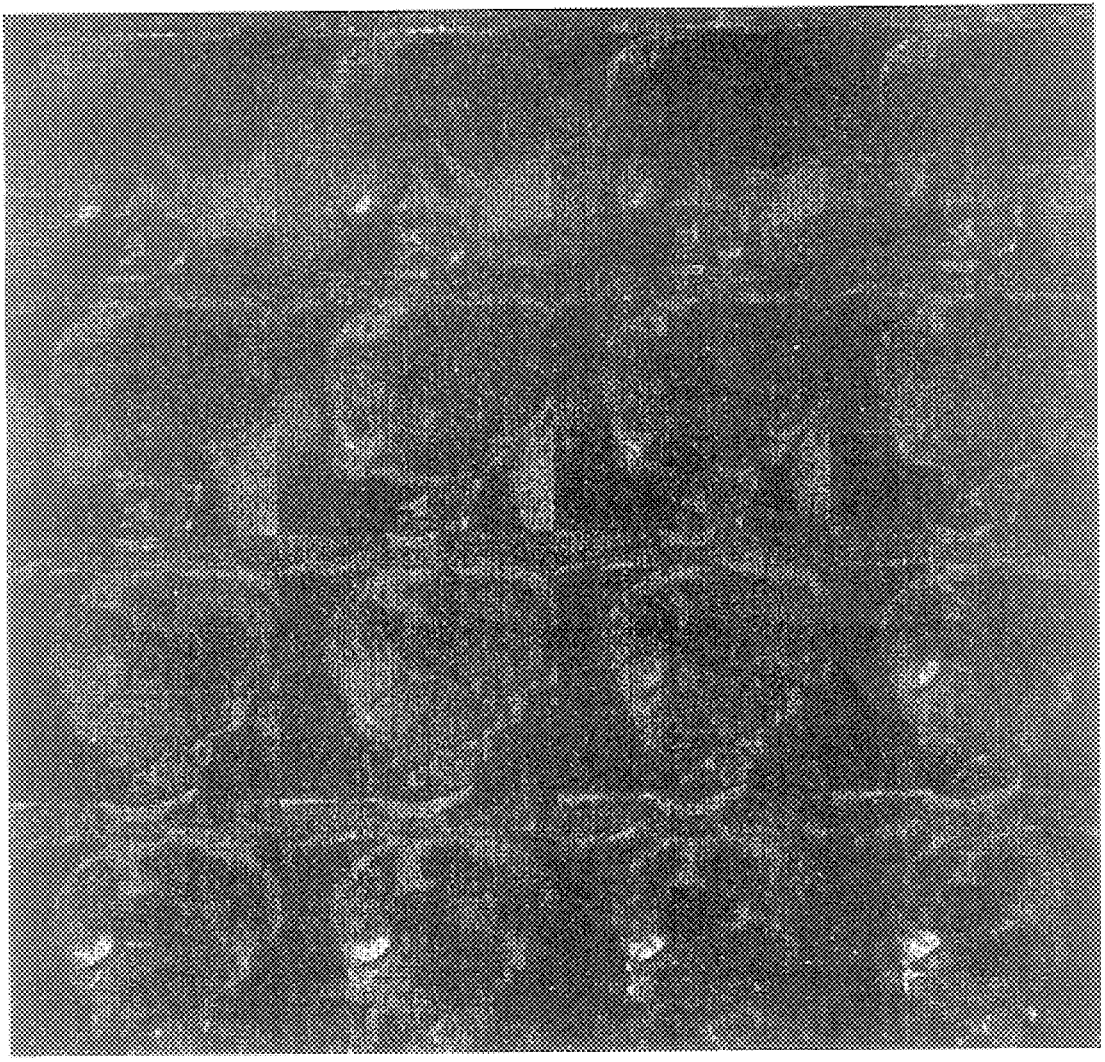
FIG. 5 illustrates sixteen images from a single point during the cardiac cycle using the 3D cine acquisition of FIG. 4.

FIG. 5 shows 16 images from one time point in the cardiac cycle from a study of a human subject. These data were acquired with the above scan parameters. In addition, an axial scan plane and body coil reception were used. The imaging field-of-view (FOV) was 24 cm, and a flip angle of 20° was used for excitation. Respiratory compensation was used to reduce motion artifacts. Due to the small FOV, aliasing in the phase-encode direction was eliminated by acquiring the data with the "no phase wrap" option. The total imaging time was 6.1 min, and 16 cardiac phases were reconstructed for each section.

Figure 6:
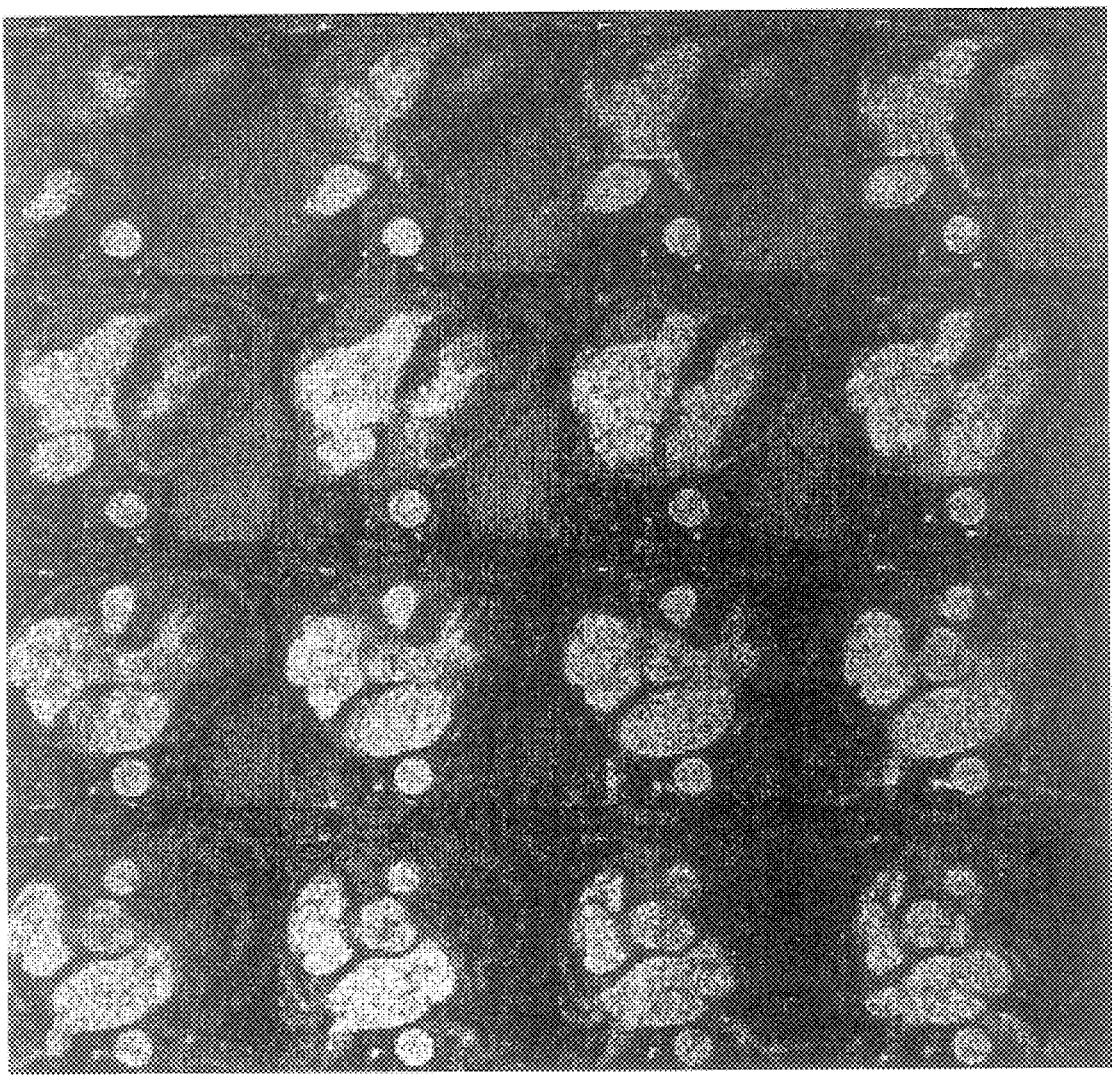
FIG. 6 illustrates a set of 16 images acquired using the 3D cine acquisition after injection of an investigational intravascular contrast agent.

Because this acquisition scheme uses a short sequence TR and volume excitation the inherent contrast between the heart muscle and the blood is poor. This problem can be overcome with the use of a $T_1$ shortening agent. Since contrast between blood and the myocardium is no longer flow dependent, it is more stable throughout the heart cycle. This is shown in a set of images in FIG. 6. These data were acquired using the same protocol as above, but in this case the sequence was run after the administration of an investigational intravascular contrast agent. In this case excellent contrast is seen between the blood and myocardium, and the endocardial border is well visualized throughout the entire cycle. This is an advantage over the traditional cine approach, where contrast definition is lost towards end diastole as the blood becomes increasingly saturated.

If a $T_1$ shortening agent such as Gd-DTPA is used in this way, more consistent contrast between blood and myocardium can be obtained, and automated image analysis should be simplified.

An advantage of the 3D imaging mode is that zero-filling can be used to produce spatial interpolation between slices. In addition, the data can be reformatted in any plane.

The scan time needed to image the entire heart with this sequence is short, but too long for breath-holding. However, respiratory gating could be used and the scan time would still be clinically acceptable.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A method of temporally resolved three dimensional dynamic magnetic resonance data acquisitions for an object with substantially cyclical motion comprising the steps of:
   a) placing the object in a static magnetic field;
   b) applying an RF excitation pulse followed by in-plane phase encode and slice direction phase encode gradients;
   c) detecting magnetic resonance signals in the presence of read-out gradients;
   d) repeating steps b) and c) for different values of slice direction phase encode gradients during a first cycle of motion of the object, while employing at least one amplitude of the in-plane phase encode gradient;
   e) repeating step d) for a time period greater than one minute over a plurality of motion cycles with other amplitudes of in-phase encode gradients;
   f) applying a phase encode rewinder gradient after each step of detecting magnetic resonance signals to reduce artifacts;
   g) applying crusher gradients before applying an RF excitation pulse to improve suppression of static tissue signals; and
   h) applying a contrast agent which alters the relaxation time of blood during the acquisition time to improve contrast in detected signals.

2. The method as defined by claim 1 wherein first-order moment nulling is avoided to reduce the echo time.

3. The method as defined by claim 1 wherein the RF pulse is on the order of 600 $\mu$s in duration with a flip angle on the order of 20°.

4. A method for temporally resolved three dimensional magnetic resonance data acquisitions for an object with cyclical motion comprising the steps of:
   a) placing the object in a static magnetic field;
   b) applying an RF excitation pulse followed by in-plane phase encode and slice direction phase encode gradients;
   c) detecting magnetic resonance signals in the presence of read-out gradients;
   d) repeating steps b) and c) for different values of in-plane phase encode gradients during a first cycle of motion of the object, while employing at least one amplitude of the slice direction phase encode gradient;
   e) repeating step d) for a time period greater than 72 seconds over a plurality of motion cycles with other amplitudes of in-phase encode gradients;
   f) applying a phase encode rewinder gradient after each step of detecting magnetic resonance signals to reduce artifacts;
   g) applying crusher gradients before applying an RF excitation pulse to improve suppression of static tissue signals; and
   h) applying a contrast agent which alters the relaxation time of blood during the acquisition time to improve contrast in the detected signals.

5. The method as defined by claim 4 wherein first-order moment nulling is avoided to reduce the echo time.

6. The method as defined by claim 4 wherein the RF pulse is on the order of 600 $\mu$s in duration with a flip angle on the order of 20°.

7. Magnetic resonance imaging apparatus for obtaining temporally resolved three dimensional magnetic resonance data for an object with cyclical motion comprising:
   a) means for applying a static magnetic field through the object along one axis;
   b) means for applying slice direction phase encode gradients and in-plane phase encode gradients to the object;
   c) means for applying an RF excitation pulse to the object followed by said gradients;
   d) means for detecting magnetic resonance signals in the presence of read-out gradients;
   said apparatus repeating the application of RF excitation pulses and the detecting of magnetic resonance signals for different values of slice direction phase encode gradients during each cycle of motion of the object while employing at least one amplitude of the in-plane phase encode gradient constant during each cycle of motion of the object;
   e) means for applying an in-plane phase encode rewinder gradient after each step of detecting nuclei relaxation signals to reduce artifacts;
   f) means for applying crusher gradients before applying an RF excitation pulse to improve suppression of static tissue relaxation time;
   wherein the RF pulse is on the order of 600 $\mu$s in duration with a flip angle on the order of 20°.

8. The apparatus as defined by claim 7 wherein the time between repetitions of RF excitation pulses is no more than 10 ms.

9. Magnetic resonance imaging apparatus for obtaining temporally resolved three dimensional magnetic resonance data for an object with cyclical motion comprising:
   a) means for applying a static magnetic field through the object along one axis;
   b) means for applying slice direction phase encode gradients and in-plane phase encode gradients to the object;
   c) means for applying an RF excitation pulse to the object followed by said gradients, wherein the RF pulse is on the order of 600 $\mu$s in duration with a flip angle on the order of 20°;
   d) means for detecting magnetic resonance signals;
   e) means for applying an in-plane phase encode rewinder gradient after each step of detecting magnetic resonance signals to reduce artifacts;

f) means for applying crusher gradients before applying an RF excitation pulse to improve suppression of static tissue relaxation time;

and said apparatus repeating the application of RF excitation pulses and the detecting of magnetic resonance signals for different values of in-plane phase encode gradient constant during each cycle of motion of the object while employing at least one amplitude of slice direction phase encode gradients.

10. A method of temporally resolving three dimensional magnetic resonance data acquisitions for an object with substantially cyclical motion comprising the steps of:

a) placing the object in a static magnetic field;

b) administering a contrast agent which alters the relaxation time during the acquisition time of at least some components of the object;

c) applying an RF excitation pulse followed by in-plane phase encode and slice direction phase encode gradients;

d) detecting magnetic resonance signals in the presence of a read-out gradient; and e) repeating steps c) and d) for different values of slice direction phase encode gradients during a first cycle of motion of the object, while employing at least one amplitude of the in-plane phase encode gradient; and f) repeating step d) for a time period greater than one minute over a plurality of motion cycles with other amplitudes of in-phase encode gradients.

11. The method as defined by claim 10 and further including the steps of:

g) applying a phase encode rewinder gradient after each step of detecting magnetic resonance signals to reduce artifacts; and h) applying crusher gradients before applying an RF excitation pulse to improve suppression of static tissue signals.

* * * * *

UNITED STATES PATENT AND TRADEMARK OFFICE
CERTIFICATE OF CORRECTION

| | | |
|---|---|---|
| PATENT NO. | : 6,185,447 B1 | Page 1 of 1 |
| APPLICATION NO. | : 09/049281 | |
| DATED | : February 6, 2001 | |
| INVENTOR(S) | : Alley et al. | |

It is certified that error appears in the above-identified patent and that said Letters Patent is hereby corrected as shown below:

Column 1:

Replace lines 5-7 with:

-- FEDERALLY-SPONSORED RESEARCH OR DEVELOPMENT
This invention was made with Government support under contract DK009232 awarded by the National Institutes of Health. The Government has certain rights in this invention. --

Signed and Sealed this

Nineteenth Day of April, 2011

David J. Kappos
*Director of the United States Patent and Trademark Office*